United States Patent
Zhong et al.

(10) Patent No.: US 11,149,016 B2
(45) Date of Patent: Oct. 19, 2021

(54) S-SUBSTITUTED-2-AMINO-3-MERCAPTOPROPIONATE DERIVATIVE, PREPARATION METHOD AND APPLICATION THEREOF

(71) Applicant: JIANGSU TASLY DIYI PHARMACEUTICAL CO., LTD., Jiangsu (CN)

(72) Inventors: Jun Zhong, Jiangsu (CN); Guocheng Wang, Jiangsu (CN)

(73) Assignee: Jiangsu Tasly Diyi Pharmaceutical Co., Ltd., Jiangsu (CN)

(*) Notice: Subject to any disclaimer, the term of this patent is extended or adjusted under 35 U.S.C. 154(b) by 330 days.

(21) Appl. No.: 16/303,786

(22) PCT Filed: May 22, 2017

(86) PCT No.: PCT/CN2017/085321
§ 371 (c)(1),
(2) Date: Nov. 21, 2018

(87) PCT Pub. No.: WO2017/202266
PCT Pub. Date: Nov. 30, 2017

(65) Prior Publication Data
US 2020/0317632 A1     Oct. 8, 2020

(30) Foreign Application Priority Data
May 25, 2016  (CN) .......................... 201610356441.4

(51) Int. Cl.
C07D 339/04   (2006.01)
C07C 323/58   (2006.01)

(52) U.S. Cl.
CPC .......... *C07D 339/04* (2013.01); *C07C 323/58* (2013.01)

(58) Field of Classification Search
CPC .......................... C07D 339/04; C07C 323/58
See application file for complete search history.

(56) References Cited

U.S. PATENT DOCUMENTS

2018/0134708 A1* 5/2018 Pasternak ............ A61K 31/438

FOREIGN PATENT DOCUMENTS

| CN | 102078327 A | 6/2011 |
| CN | 104974154 A | 10/2015 |
| KR | 101511056 B1 | 4/2015 |

OTHER PUBLICATIONS

Struthers et al. Chem Eur. J. 2008, 14, 6173-6183 (Year: 2008).*
NIH, Preventing Alzheimer's Disease: What Do We Know? Obtained from https://www.nia.nih.gov/health/preventing-alzheimers-disease-what-do-we-know on Dec. 30, 2020 (Year: 2020).*
Mucke et al. Nature, 2009, 461, 895-897 (Year: 2009).*
Zhu et al. PLoS One, 2015, 10(4) pp. 1-14 (Year: 2015).*
Makoto Ouchi et. al., Selective Single Monomer Radical Addition via Template-Assisted Ring Closure: A Feasibility Study toward Sequence Control in Vinyl Polymers with Peptide Templates, Journal, Sep. 22, 2014, pp. 149-160. Washington DC.
Harriet Struthers et al., Click-to-chelate Design and Incorporation of Triazole-Containing Metal Chelating Systems into Biomolecules of Diagnostic and Therapeutic Interest, Chem. Eur. Journal, May 21, 2008, pp. 6173-6183.
International Search Report from PCT/CN2017/085321 dated Aug. 11, 2017.
Extended European Search Report from EP17802112.7 dated Jan. 17, 2020.
Widanapathirana et al., "Tuning Nanopore Formation of Oligocholate Macrocycles by Carboxylic Acid Dimerization in Lipid Membranes"; Journal of Organic Chemistry, 78(9):, May 3, 2013, pp. 4610-4614.
Zhu et al., "The Novel Analogue of Hirsutine as an Anti-Hypertension and Vasodilatary Agent Both In Vitro and In Vivo"; PLOS One, 10(4):, Apr. 24, 2015, p. 1-9.
Wen et al., "The Pharmacological Effects of S-Propargyl-Cysteine, a Novel Endogenous H2S-Producing Compound":, Dec. 13, 2015 (Dec. 13, 2015), pp. 325-336.

* cited by examiner

*Primary Examiner* — Matthew P Coughlin
(74) *Attorney, Agent, or Firm* — Dilworth & Barrese, LLP

(57) ABSTRACT

The present invention relates to a S-substituted-2-amino-3-mercaptopropionate derivative, a preparation method and an application thereof. The S-substituted-2-amino-3-mercaptopropionate derivative in the present invention has a structure of a formula (A). The present invention also includes an application of the S-substituted-2-amino-3-mercaptopropionate derivative serving as a medicine for treating and/or preventing neurodegenerative diseases, particularly Alzheimer's disease.

Formula (A)

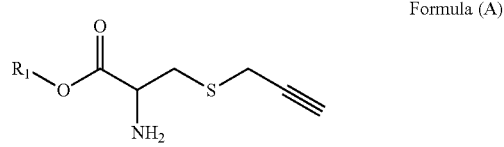

8 Claims, No Drawings

S-SUBSTITUTED-2-AMINO-3-MERCAPTOPROPIONATE DERIVATIVE, PREPARATION METHOD AND APPLICATION THEREOF

This application claims priority to Chinese Patent Application No. CN201610356441.4 filed on May 25, 2016.

TECHNICAL FIELD

The present invention relates to the fields of organic chemistry and medicinal chemistry, and more particularly, to a S-substituted-2-amino-3-mercaptopropionate derivative, a preparation method and application thereof, as well as an application in preparation of medicines for treating and/or preventing neurodegenerative diseases, particularly Alzheimer's disease.

BACKGROUND ART

Central nervous system degenerative diseases are a group of chronic progressive nervous system diseases based on primary neuronal degeneration. These diseases mainly include Alzheimer's disease, Parkinson's disease (PD), Huntington's disease, amyotrophic lateral sclerosis, spinal muscular atrophy and the like.

Alzheimer's disease is a progressive degenerative disease of a central nervous system and includes main clinical manifestations such as progressive memory loss, losses of learning ability and living ability, social function withdrawal, mental behavior disorder and the like. Alzheimer's disease severely destroys health of middle-aged and aged people, while patients suffering from Alzheimer's disease unrelentingly torture relatives and caregivers, thereby bringing huge mental and economical burdens to the family and society. However, an effective measure to prevent and treat Alzheimer's disease does not exist up to now, largely because of complexity of etiology and pathogenesis of Alzheimer's disease. The pathogenesis of most of the patients is still unclear. Gene differences may be found from 1%-5% of patients only. Since discovery of Alzheimer's disease in 1907, several pieces of different hypothesis try to explain the pathogenesis of Alzheimer's disease as follows: choline hypothesis, amyloid protein hypothesis, microtubule-associated protein hypothesis and the like, but none has been widely acceptable at present. Moreover, medicines developed according to main theories such as cholinergic neuron abnormality, metabolic disturbance of amyloid protein (Aβ cascade reaction) by domestic and foreign scholars and treatment performed cannot restrain occurrence and deterioration of Alzheimer's disease, which indicates that Alzheimer's disease is an extremely complex disease entity. In recent ten years, some researchers have found that, in addition to metabolic disturbance of endogenous nitric oxide (NO) in brains of patients suffering from Alzheimer's disease, content of endogenous hydrogen sulfide ($H_2S$) is obviously decreased and directly proportional to severity of dementia. Thus, there is a surge of study on physiological functions and pathogenesis of the endogenous $H_2S$ and study on relevance of the $H_2S$ to neurodegenerative disease, particularly Alzheimer's disease.

The endogenous hydrogen sulfide ($H_2S$) is a novel gas signal molecule discovered after NO and CO. Researches in recent over 20 years have revealed that the $H_2S$ has important physiological functions in the central nervous system, such as an effect of preventing nerve cells and tissues from suffering from inflammations, cell apoptosis, oxidative stress injury and the like caused by β-amyloid protein (Aβ), lipopolysaccharide, homocysteine, MPP+ and the like. The $H_2S$ achieves important neuromodulator and neuroprotective effects. In vitro and in vivo experiments show that, reduction of a $H_2S$ level may cause dysfunctions of multiple metabolic pathways, cell damage and other histopathologic changes. After the endogenous $H_2S$ is supplemented, pathological changes and clinical manifestations are obviously improved, which indicates that the $H_2S$ may participate in a pathogenetic process of the neurodegenerative disease. Clinical test discovers that, the level of the $H_2S$ in bodies of patients with senile dementia and some patients suffering from the neurodegenerative diseases is obviously decreased, and the change of the $H_2S$ level is related to severity of the illness.

The clinical tests and experiments prove that the $H_2S$ concentration in brains of the patients with senile dementia is decreased. The in vitro and in vivo experiments discover that, a decrease of the $H_2S$ content may cause oxidative stress injury, Aβ cascade reaction, neuronal apoptosis and the like in model animals. A supplement of an exogenous $H_2S$ donor may enable related neurotransmitter and neuropathological changes of Alzheimer's disease to be obviously improved. S-propargyl-cysteine (SPRC) has a molecular formula of $C_6H_9O_2NS$, has a structural formula shown as a formula (I) and is an $H_2S$ donor. The SPRC has applications in various aspects such as immune-associated inflammations, cardiovascular system inflammations, digestive system neoplasm, central nervous system diseases, myocardial damage and the like.

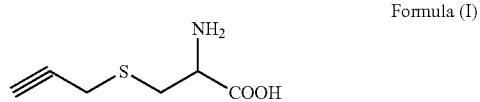

Formula (I)

In addition, gastrodin is a main component of traditional Chinese medicine rhizoma gastrodiae, with a positive effect of treating diseases of the central nervous system and cardiovascular system, thus being a common medicine for treating stroke and also used for improving learning and memory functions and treating Alzheimer's disease in Japan. Therefore, an in-vivo metabolite of the gastrodin, i.e., p-hydroxybenzylalcohol (shown as a formula (IIIc) is combined with the $H_2S$ donor SPRC, and on this basis, a series of novel compounds are developed and expected to enhance treatment effects.

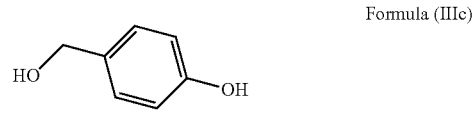

Formula (IIIc)

SUMMARY OF THE INVENTION

It's an object of the present invention to provide a novel S-substituted-2-amino-3-mercaptopropionate derivative or a medicinal acid addition salt, a solvate, a polymorphism, an enantiomer or a racemic mixture thereof.

Specifically, the S-substituted-2-amino-3-mercaptopropionate derivative in the present invention has a structure of a formula (A) as follows:

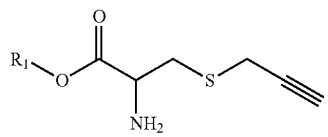

Formula (A)

wherein R₁ is selected from

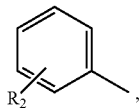

substituted or unsubstituted alkyl, alkoxy, aralkyl, alkoxy aryl, alkyl nitrate and aryl alkanol, and R₂ is selected from substituted or unsubstituted heterocyclyl, alkyl ester, alkyl carbonyl and alkane hydroxyl.

Preferably, R₁ is selected from

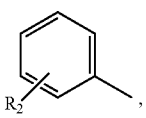

substituted or unsubstituted C1-C10 linear or branched alkyl, C1-C10 alkoxy, C7-C20 aralkyl, C7-C20 alkoxy aryl, C1-C10 alkyl nitrate and C7-C20 aryl alkanol, and R₂ is selected from substituted or unsubstituted 4-7-membered heterocyclyl, C1-C10 alkyl ester, C1-C10 alkyl carbonyl and C1-C10 alkane hydroxyl.

More preferably, R₁ is further selected from

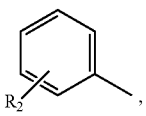

C7-C20 aralkyl and C1-C6 alkyl nitrate, and R₂ is selected from 4-7-membered heterocyclothione, S-substituted-2-amino-3-mercaptopropionate, C1-C6 alkyl carbonyl and C1-C6 alkane hydroxyl. The S-substituted-2-amino-3-mercaptopropionate derivative in the present invention specifically includes compounds as follows:

Va

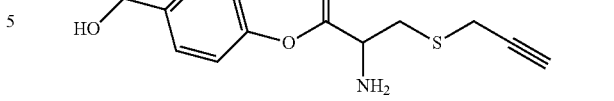

Vb

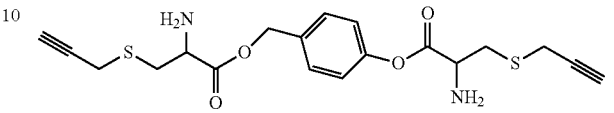

Vc

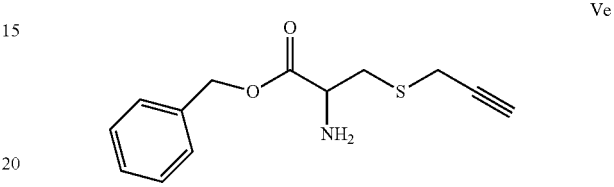

Vd

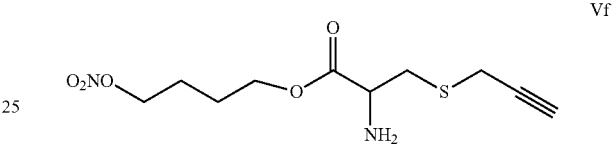

Ve

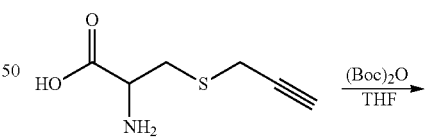

Vf

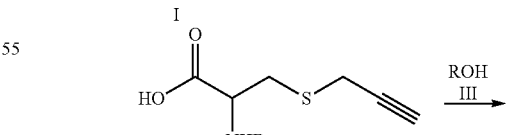

The present invention further provides a medicinal acid addition salt of the S-substituted-2-amino-3-mercaptopropionate derivative. The salt may be salt formed by the S-substituted-2-amino-3-mercaptopropionate derivative and sulfuric acid, hydrochloric acid, hydrobromic acid, phosphoric acid, tartaric acid, fumaric acid, maleic acid, citric acid, acetic acid, formic acid, methanesulfonic acid, p-toluenesulfonic acid, oxalic acid or succinic acid.

Another purpose of the present invention is to provide a preparation method of the S-substituted-2-amino-3-mercaptopropionate derivative or the medicinal acid addition salt, the solvate, the polymorphism, the enantiomer or the racemic mixture or a pharmaceutical composition thereof.

The preparation method of the S-substituted-2-amino-3-mercaptopropionate derivative in the present invention includes the following reaction steps:

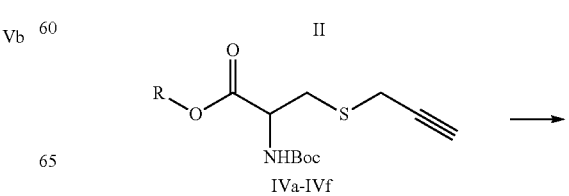

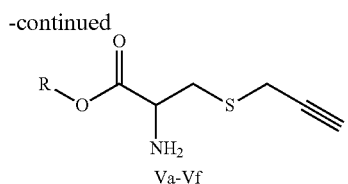

wherein, ROH is selected from compounds as follows:

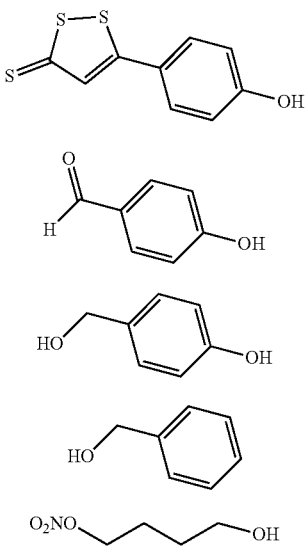

It's another object of the present invention to provide a pharmaceutical composition taking the S-substituted-2-amino-3-mercaptopropionate derivative or the medicinal acid addition salt, solvate, polymorphism, enantiomer or racemic mixture thereof as active ingredients.

The pharmaceutical composition may include pharmaceutically acceptable carriers according to needs. The pharmaceutically acceptable inert carriers may be solid or liquid. The carriers can be prepared into solid or semisolid pharmaceutical preparations in forms of powder, tablets, dispersible powder, capsules, suppository and adhesive paste. The solid carriers are generally used in this case. Available solid carriers are preferably one or more substances of a diluent, a flavoring agent, a solubilizer, a lubricating agent, a suspending agent, an adhesive, an expanding agent and the like, or may be encapsulating substances. In a powder preparation, 5%-70% of pelletized active ingredients are included in the carriers. Specific examples of appropriate solid carriers include magnesium carbonate, magnesium stearate, talcum powder, sucrose, lactose, pectin, dextrin, starch, gelatin, xanthan gum, methylcellulose, sodium carboxymethylcellulose, low-boiling point wax, cocoa butter and the like. Since the carriers are easy for drug administration, the tablets, powder and capsules represent oral solid preparations that are the most absorbable.

Liquid preparations include solutions, suspension and emulsion. An injectable preparation in non-gastrointestinal administration may be in a form of water or a solution of water and propylene glycol, and an isotonic degree, a pH value and the like are regulated to be suitable for physiological conditions of living bodies. The liquid preparations may further be prepared into a form of an aqueous solution of polyethylene glycol. An oral aqueous solution may be prepared by dissolving the active ingredients into water and adding the appropriate coloring agent, flavoring agent, stabilizer and thickening agent. The pelletized active ingredients may be dispersed in sticky substance such as natural or synthetic rubber, methylcellulose, acidic sodium methyl cellulose and other known suspending agents to prepare aqueous suspension to be orally taken.

In order to realize easy drug administration and uniform dose, preparation of the above pharmaceutical preparation into a dose unit form is particularly favorable. The dose unit form of the preparation is a physical separation unit suitable to serve as a single dose, and each unit includes active ingredients in a calculated preset amount capable of achieving an expected treatment effect. Such a dose unit form may be in a packaged form, such as tablets, capsules or powder filled in a small tube or bottle, or ointments, gel or cream filled in the tube or bottle. Although the amount of the active ingredients included in the dose unit form can change, the amount is generally regulated in a range of 1-1000 mg according to efficacy of the selected active ingredients.

Those skilled in the art may determine an optimal dose suitable for a certain condition according to a conventional method. Generally, a dose used when treatment starts is lower than the optimal dose of the active ingredients, and the administration dose is gradually increased until an optimal treatment effect is achieved. For convenience, a total daily dose may be divided into several parts, and drug administration is performed in several times.

It's another object of the present invention to provide an application of the S-substituted-2-amino-3-mercaptopropionate derivative or the medicinal acid addition salt, solvate, polymorphism, enantiomer or racemic mixture thereof or a pharmaceutical composition including the S-substituted-2-amino-3-mercaptopropionate derivative or the medicinal acid addition salt, solvate, polymorphism, enantiomer or racemic mixture thereof in preparation of medicines for treating and/or preventing a neurodegenerative disease.

Preferably, the neurodegenerative disease is senile dementia.

More preferably, the senile dementia is Alzheimer's disease.

In the present invention, by virtue of passive avoidance response experiments of mice, influences of the S-substituted-2-amino-3-mercaptopropionate derivative on learning and memory functions of the model are observed. The results show that the S-substituted-2-amino-3-mercaptopropionate derivative can decrease a trend of error times of mice with memory impairment entering a darkroom and increase a trend of latency of the mice with memory impairment entering the darkroom, which indicates that the S-substituted-2-amino-3-mercaptopropionate derivative may serve as a therapeutic drug to be applied to the senile dementia such as Alzheimer's disease and other neurodegenerative diseases.

DETAILED DESCRIPTION OF THE INVENTION

Embodiments below are used for further illustrating the present invention, rather than limiting the present invention.

Embodiment 1

2-(t-butyloxycarbonylamino)-3-propinyl mercaptopropionic acid (II)

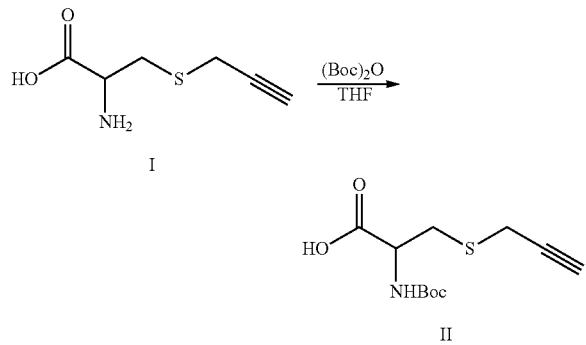

There are steps of: dissolving 25 g of 2-amino-3-propinyl mercaptopropionic acid I into 250 mL of tetrahydrofuran, adding 35 g of di-tert-butyl dicarbonate ester, stirring to be uniform, adding 500 mL of saturated sodium bicarbonate solution, heating to 50° C. and reacting for 12 hours, cooling, neutralizing with 1M of diluted hydrochloric acid until a pH value is equal to 7; extracting with ethyl acetate, drying an organic phase with anhydrous sodium sulfate, filtering and removing a drying agent, and evaporating to dryness, thereby obtaining 35 g of a light yellow oily matter 2-(t-butyloxycarbonylamino)-3-propinyl mercaptopropionic acid (II) having a yield of 86%.

$^1$H NMR (400 MHz, DMSO): δ 12.78 (s, 1H), 7.16 (d, 1H), 4.13-4.09 (m, 1H), 3.39-3.37 (m, 2H), 3.17-3.16 (m, 1H), 3.07-3.02 (m, 1H), 2.84-2.79 (m, 1H), 1.39 (s, 9H). MS: m/z 258 [M−1]$^-$.

Embodiment 2

2-(t-butyloxycarbonylamino)-3-propinylmercaptopropionic acid-4-(3-thio-3H-1,2-dithio-5-alkenyl) phenol ester (IVa)

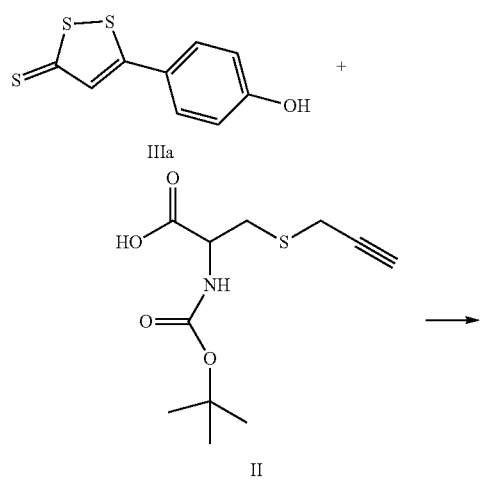

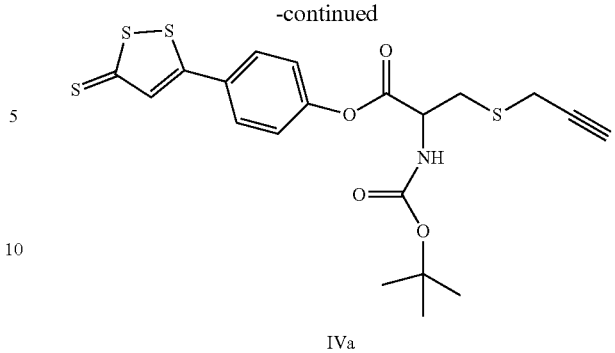

There are steps of: dissolving 3 g of 2-(t-butyloxycarbonylamino)-3-propinyl mercaptopropionic acid II, 1 g of 4-(3-thio-3H-1,2-dithio-5-alkenyl) phenol IIIa and 4 g of HBTU into 50 mL of tetrahydrofuran, slowly dripping 2 mL of triethylamine into a reaction solution, and reacting at a room temperature for 12 hours; adding 100 mL of water, extracting with ethyl acetate, washing an organic phase with 1M of diluted hydrochloric acid, a saturated sodium bicarbonate solution and a saturated sodium chloride solution in sequence, and drying the organic phase with anhydrous sodium sulfate; filtering and removing a drying agent, evaporating to dryness, and performing column chromatography (a ratio of petroleum ether to ethyl acetate is 4:1), thereby obtaining 1.1 g of 2-(t-butyloxycarbonylamino)-3-propinylmercaptopropionic acid-4-(3-thio-3H-1,2-dithio-5-alkenyl) phenol ester (IVa) having a yield of 53%.

$^1$H NMR (400 MHz, DMSO): δ 8.02 (d, 2H), 7.83 (s, 1H), 7.73 (d, 1H), 7.31-7.29 (m, 2H), 4.49-4.44 (m, 1H), 3.48 (s, 2H), 3.24 (s, 2H), 3.08-3.02 (m, 1H), 1.43 (s, 9H), MS: m/z 468 [M+H]$^+$.

Embodiment 3

2-amino-3-propinylmercaptopropionic acid-4-(3-thio-3H-1,2-dithio-5-alkenyl) phenol ester (Va)

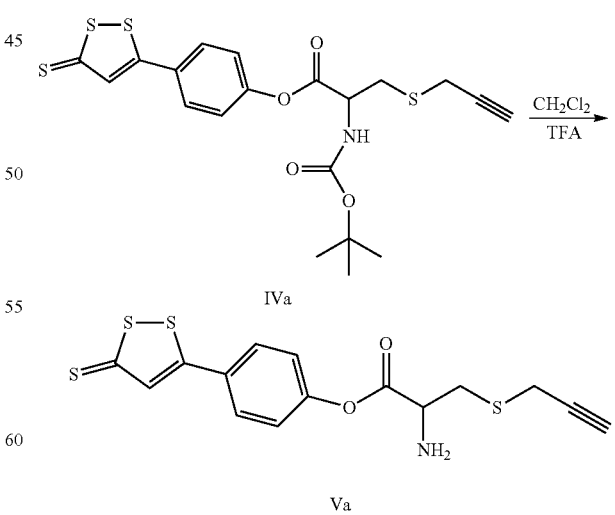

There are steps of: dissolving 0.5 g of 2-(t-butyloxycarbonylamino)-3-propinylmercaptopropionic acid-4-(3-thio-3H-1,2-dithio-5-alkenyl) phenol ester (IVa) into 20 mL of dichloromethane, adding 2 mL of trifluoroacetic acid, and reacting at a room temperature for 6 hours; adding 3N of hydrochloric acid, continuously stirring for 2 hours, separating a water layer, evaporating water to dryness, and performing column chromatography (a ratio of dichloromethane to methanol is 10:1), thereby obtaining 0.23 g of 2-amino-3-propinylmercaptopropionic acid-4-(3-thio-3H-1,2-dithio-5-alkenyl) phenol ester (Va) having a yield of 60%.

$^1$H NMR (400 MHz, DMSO): δ 9.19 (s, 3H), 8.05-8.03 (m, 2H), 7.84 (s, 1H), 7.45-7.43 (m, 2H), 4.63-4.60 (m, 1H), 3.59-3.56 (m, 2H), 3.37-3.31 (m, 3H), MS: m/z 368 [M+H]$^+$.

Embodiment 4

2-(t-butyloxycarbonylamino)-3-propinylmercaptopropionic acid-4-formyl phenol ester (IVb)

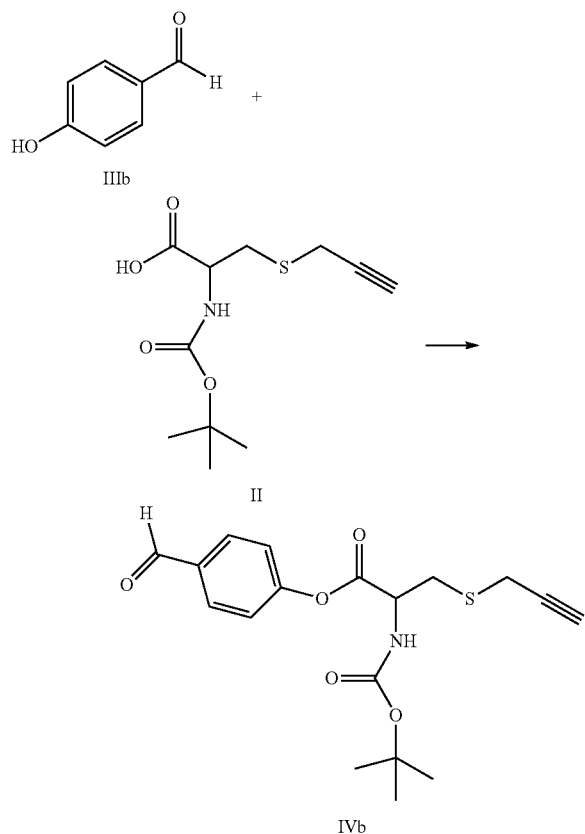

There are steps of: dissolving 3 g of 2-(t-butyloxycarbonylamino)-3-propinyl mercaptopropionic acid II, 2 g of 4-hydroxybenzaldehyde IIIb and 5 g of HBTU into 50 mL of tetrahydrofuran, adding 2 mL of triethylamine, and reacting at a room temperature for 12 hours; adding 100 mL of water, extracting with ethyl acetate, washing an organic phase with 1M of diluted hydrochloric acid, a saturated sodium bicarbonate solution and a saturated sodium chloride solution in sequence, and drying the organic phase with anhydrous sodium sulfate; filtering and removing a drying agent, evaporating to dryness, and performing column chromatography (a ratio of petroleum ether to ethyl acetate is 3:1), thereby obtaining 3.6 g of 2-(t-butyloxycarbonylamino)-3-propinylmercaptopropionic acid-4-formyl phenol ester (IVb) having a yield of 85%.

$^1$H NMR (400 MHz, DMSO): δ 10.01 (s, 1H), 8.03 (d, 2H), 7.73 (d, 1H), 7.37 (d, 2H), 4.49-4.44 (m, 1H), 3.48-3.47 (m, 2H), 3.24-3.18 (m, 2H), 3.07-3.01 (m, 1H), 1.42 (s, 9H), MS: m/z 464 [M+H]$^+$.

Embodiment 5

2-amino-3-propinylmercaptopropionic acid-4-formyl phenol ester (Vb)

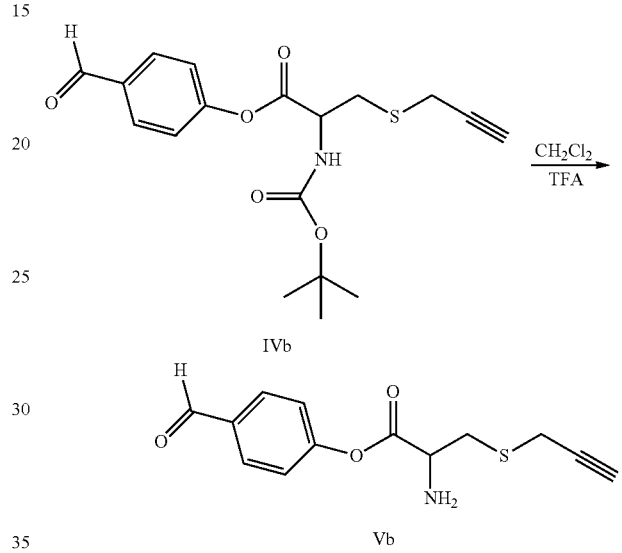

There are steps of: dissolving 0.5 g of 2-(t-butyloxycarbonylamino)-3-propinylmercaptopropionic acid-4-formyl phenol ester (IVb) into 20 mL of dichloromethane, adding 2 mL of trifluoroacetic acid, and reacting at a room temperature for 6 hours; adding 3N of hydrochloric acid, continuously stirring for 2 hours, separating a water layer, evaporating water to dryness, and performing column chromatography (a ratio of dichloromethane to methanol is 10:1), thereby obtaining 0.28 g of 2-amino-3-propinylmercaptopropionic acid-4-formyl phenol ester (Vb) having a yield of 76%.

$^1$H NMR (400 MHz, DMSO): δ 10.04 (s, 1H), 9.18 (s, 3H), 8.04-8.03 (m, 2H), 7.83 (s, 1H), 7.46-7.45 (m, 2H), 4.62-4.61 (m, 1H), 3.61-3.57 (m, 2H), 3.38-3.30 (m, 3H), MS: m/z 264 [M+H]$^+$.

Embodiment 6

2-(t-butyloxycarbonylamino)-3-propinylmercaptopropionic acid-4-benzyl alcohol phenol ester (IVc)

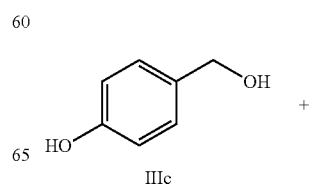

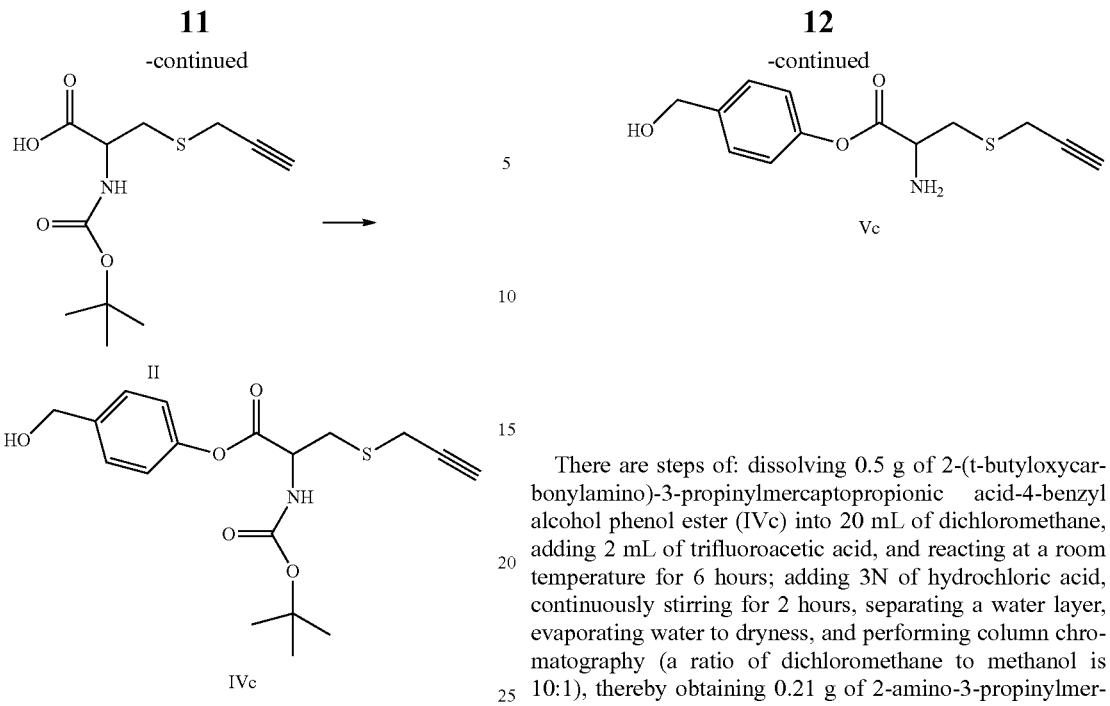

There are steps of: dissolving 3 g of 2-(t-butyloxycarbonylamino)-3-propinyl mercaptopropionic acid II, 4 g of p-hydroxybenzylalcohol IIIc and 6 g of HBTU into 25 mL of tetrahydrofuran, slowly dripping 3 mL of triethylamine into a reaction solution, and reacting at a room temperature for 12 hours; adding 100 mL of water, extracting with ethyl acetate, washing an organic phase with 1M of diluted hydrochloric acid, a saturated sodium bicarbonate solution and a saturated sodium chloride solution in sequence, and drying the organic phase with anhydrous sodium sulfate; filtering and removing a drying agent, evaporating to dryness, and performing column chromatography (a ratio of petroleum ether to ethyl acetate is 5:1), thereby obtaining 3.0 g of 2-(t-butyloxycarbonylamino)-3-propinylmercaptopropionic acid-4-benzyl alcohol phenol ester (IVc) having a yield of 70%.

¹H NMR (400 MHz, DMSO): δ 7.65-7.63 (d, 1H), 7.38-7.36 (d, 2H), 7.07-7.05 (d, 1H), 5.26-5.24 (m, 1H), 4.51-4.50 (m, 2H), 4.45-4.36 (m, 1H), 3.47 (brs, 2H), 3.23-3.21 (m, 1H), 3.19-3.16 (m, 1H), 3.05-2.99 (m, 1H), 1.42 (s, 9H), MS: m/z 366 [M+H]⁺.

Embodiment 7

2-amino-3-propinylmercaptopropionic acid-4-benzyl alcohol phenol ester (Vc)

There are steps of: dissolving 0.5 g of 2-(t-butyloxycarbonylamino)-3-propinylmercaptopropionic acid-4-benzyl alcohol phenol ester (IVc) into 20 mL of dichloromethane, adding 2 mL of trifluoroacetic acid, and reacting at a room temperature for 6 hours; adding 3N of hydrochloric acid, continuously stirring for 2 hours, separating a water layer, evaporating water to dryness, and performing column chromatography (a ratio of dichloromethane to methanol is 10:1), thereby obtaining 0.21 g of 2-amino-3-propinylmercaptopropionic acid-4-benzyl alcohol phenol ester (Vc) having a yield of 57%.

¹H NMR (400 MHz, CD₃OD): δ 7.47-7.45 (m, 2H), 7.24-7.22 (m, 2H), 4.71-4.69 (m, 1H), 4.65 (brs, 2H), 3.59-3.52 (m, 3H), 3.43-3.37 (m, 1H), 2.83-2.82 (m, 1H), MS: m/z 266 [M+H]⁺.

Embodiment 8

Bis(2-(t-butyloxycarbonylamino)-3-propinylmercaptopropionic acid)-4-benzyl alcohol-1-phenol diester (IVd)

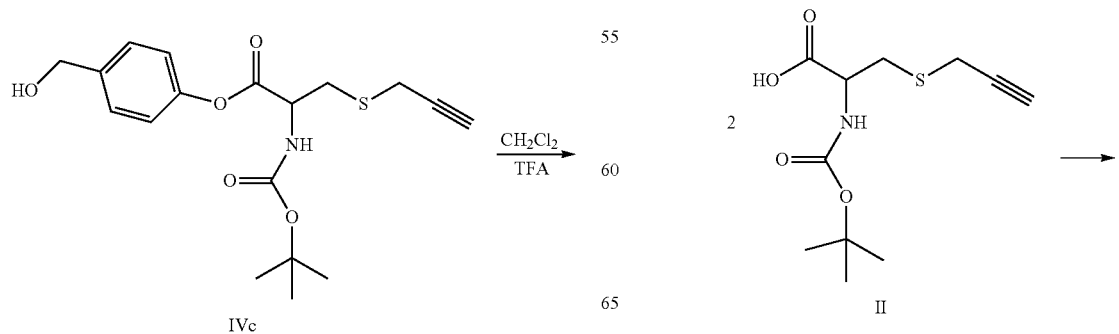

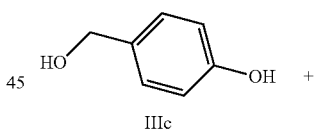

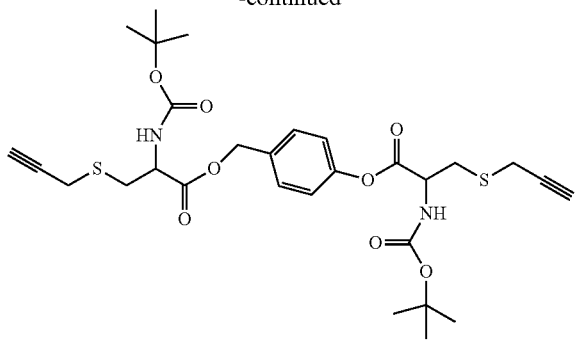

IVd

There are steps of: dissolving 6 g of 2-(t-butyloxycarbonylamino)-3-propinyl mercaptopropionic acid II, 4 g of p-hydroxybenzylalcohol IIIc and 12 g of HBTU into 100 mL of tetrahydrofuran, slowly dripping 10 mL of triethylamine into a reaction solution, and reacting at a room temperature for 12 hours; adding 100 mL of water, extracting with ethyl acetate, washing an organic phase with 1M of diluted hydrochloric acid, a saturated sodium bicarbonate solution and a saturated sodium chloride solution in sequence, and drying the organic phase with anhydrous sodium sulfate; filtering and removing a drying agent, evaporating to dryness, and performing column chromatography (a ratio of petroleum ether to ethyl acetate is 6:1), thereby obtaining 4.6 g of bis(2-(t-butyloxycarbonylamino)-3-propinylmercaptopropionic acid)-4-benzyl alcohol-1-phenol diester (IVd) having a yield of 65%.

$^1$H NMR (400 MHz, DMSO): δ 7.67-7.65 (m, 1H), 7.45-7.43 (m, 3H), 7.12-7.10 (m, 2H), 5.16 (s, 2H), 4.44-4.41 (m, 1H), 4.27-4.24 (m, 1H), 3.46 (brs, 2H), 3.40-3.39 (m, 2H), 3.23-3.16 (m, 3H), 3.09-3.05 (m, 2H), 2.90-2.85 (m, 1H), 1.42 (s, 9H), 1.38 (s, 9H), MS: m/z 607 [M+H]$^+$.

Embodiment 9 bis(2-amino-3-propinylmercaptopropionic acid)-4-benzyl alcohol-1-phenol diester (Vd)

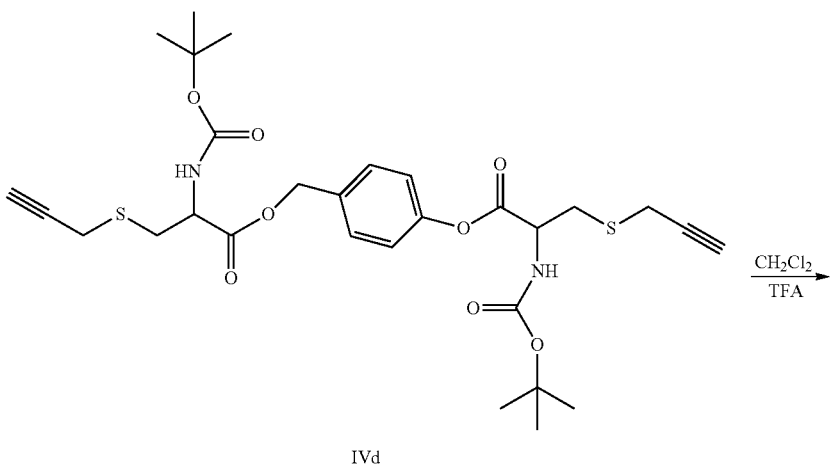

IVd

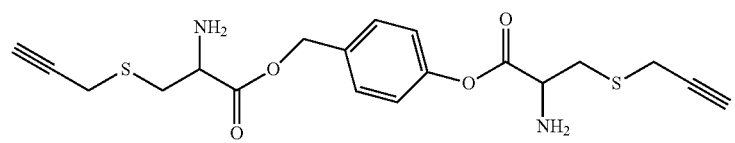

Vd

There are steps of: dissolving 0.5 g of bis(2-(t-butyloxy-carbonylamino)-3-propinylmercaptopropionic acid)-4-benzyl alcohol-1-phenol diester (IVd) into 20 mL of dichloromethane, adding 2 mL of trifluoroacetic acid, and reacting at a room temperature for 6 hours; adding 3N of hydrochloric acid, continuously stirring for 2 hours, separating a water layer, evaporating water to dryness, and performing column chromatography (a ratio of dichloromethane to methanol is 10:1), thereby obtaining 0.26 g of bis(2-amino-3-propinyl-mercaptopropionic acid)-4-benzyl alcohol-1-phenol diester (Vd) having a yield of 78%.

$^1$H NMR (400 MHz, DMSO): δ 9.17 (brs, 3H), 8.19 (brs, 3H), 7.58-7.55 (m, 2H), 7.29-7.26 (m, 2H), 5.28 (d, 1H), 4.59 (t, 1H), 4.40 (t, 1H), 4.18 (t, 1H), 3.58-3.44 (m, 5H), 3.35-3.32 (m, 2H), 3.22-3.18 (m, 2H), 3.14-3.09 (m, 1H), MS: m/z 407 [M+H]$^+$.

Embodiment 10

2-(t-butyloxycarbonylamino)-3-propinylmercapto-propionic acid-4-nitro-1-butanol ester (IVf)

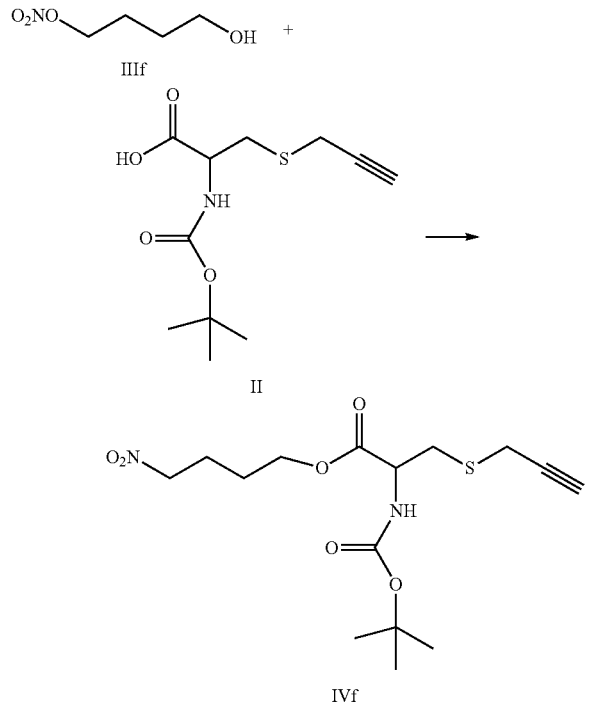

There are steps of: dissolving 3 g of 2-(t-butyloxycarbonylamino)-3-propinyl mercaptopropionic acid II, 1 g of 4-nitro-1-butanol IIIf and 4 g of HBTU into 50 mL of tetrahydrofuran, slowly dripping 2 mL of triethylamine into a reaction solution, and reacting at a room temperature for 12 hours; adding 100 mL of water, extracting with ethyl acetate, washing an organic phase with 1M of diluted hydrochloric acid, a saturated sodium bicarbonate solution and a saturated sodium chloride solution in sequence, and drying the organic phase with anhydrous sodium sulfate; filtering and removing a drying agent, evaporating to dryness, and performing column chromatography (a ratio of petroleum ether to ethyl acetate is 5:1), thereby obtaining 2.0 g of 2-(t-butyloxycarbonylamino)-3-propinylmercaptopropionic acid-4-nitro-1-butanol ester (IVf) having a yield of 48%.

$^1$H NMR (400 MHz, CDCl$_3$): δ 5.41-5.39 (m, 1H), 4.48 (brs, 1H), 4.15-4.12 (brs, 2H), 3.39-3.36 (m, 2H), 3.29-2.99 (m, 4H), 2.27-2.26 (m, 1H), 1.91-1.88 (m, 2H), 1.79-1.76 (m, 2H), 1.38 (s, 9H), MS: m/z 361 [M+H]$^+$.

Embodiment 11

2-amino-3-propinylmercaptopropionic acid-4-nitro-1-butanol ester (Vf)

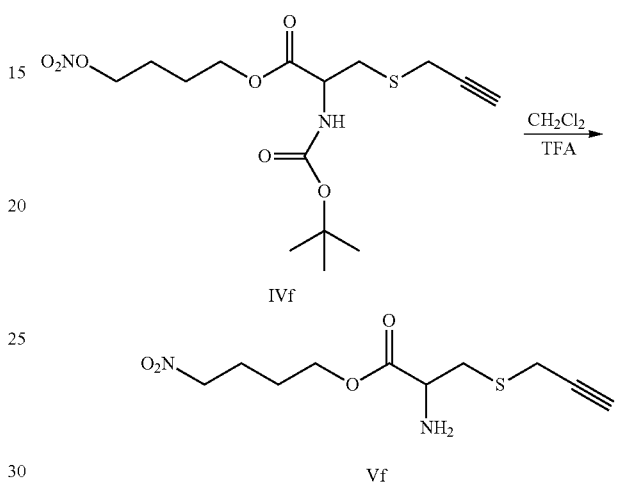

There are steps of: dissolving 0.5 g of 2-(t-butyloxycarbonylamino)-3-propinylmercaptopropionic acid-4-nitro-1-butanol ester (IVf) into 20 mL of dichloromethane, adding 2 mL of trifluoroacetic acid, and reacting at a room temperature for 6 hours; adding 3N of hydrochloric acid, continuously stirring for 2 hours, separating a water layer, evaporating water to dryness, and performing column chromatography (a ratio of dichloromethane to methanol is 10:1), thereby obtaining 0.26 g of 2-amino-3-propinylmercaptopropionic acid-4-nitro-1-butanol ester (Vf) having a yield of 72%.

$^1$H NMR (400 MHz, CDCl$_3$): δ 5.52-5.43 (m, 1H), 4.52-4.48 (m, 1H), 4.25-4.22 (m, 2H), 3.42-3.39 (m, 2H), 3.34-2.31 (m, 4H), 2.29-2.25 (m, 1H), 1.92-1.90 (m, 2H), 1.82-1.79 (m, 2H), MS: m/z 261 [M+H]$^+$.

Embodiment 12 Drug Efficacy Study on Compounds in the Present Invention

Memory functions of mice are injured by scopolamine, and effects of improvement of tested materials on the memory functions of the mice are observed.

Experimental Materials:

Animals: ICR mice, male, 20-22 g, purchased from Institute for Experimental Animals in Chinese Academy of Medical Sciences, certification number: SCXK (JING) 2014-0004.

Agent: scopolamine (J&K Company), donepezil reagent (TCI Company).

Tested materials: 4 tested materials and a positive-drug donepezil are provided by Tasly Group. Dosage of administration: administered by tested materials according to 80 mg/kg weight, administered by donepezil according to 5 mg/kg weight, an administration volume of 2 ml.

Experimental Steps of:

purchasing 60 mice, and enabling the mice to adapt to an environment for three days; dividing the mice into 6 groups randomly, wherein a blank control group includes 10 mice, the rest mice are contained in administration groups, and each administration group includes 10 mice; respectively administering the tested materials and positive drug, performing intragastric administration for 7 days, putting the mice into a darkroom to adapt to the environment on the fifth day during administration, electrifying the darkroom on the sixth day during administration, training the mice to elude the darkroom, and training each mouse once; testing on the seventh day, administering with scopolamine by 3 mg/kg within 20 minutes before testing, and recording time of the mice entering the darkroom for the first time and a number of times of the mice entering the darkroom within 3 minutes during testing.

Experimental Results:

TABLE 1

Influences of tested materials on latency and error times of mice with memory disorders caused by scopolamine entering the darkroom ($\bar{x} \pm s$, n = 10)

| Group | Latency (s) | Error times |
|---|---|---|
| Model group | 47.0 ± 55.6 | 4.6 ± 4.2 |
| Donepezil | 49.5 ± 71.6 | 6.8 ± 5.4 |
| SPRC | 50.5 ± 69.7 | 3.8 ± 4.0 |
| Va | 55.8 ± 61.3 | 4.7 ± 4.6 |
| Vb | 53.2 ± 59.4 | 4.1 ± 3.7 |
| Vc | 66.8 ± 57.1 | 2.4 ± 1.3 |
| Vd | 63.6 ± 69.5 | 2.6 ± 3.3 |
| Vf | 60.2 ± 61.3 | 2.4 ± 2.3 |

CONCLUSION

Passive avoidance response is a common method used commonly to detect learning and memory functions of small animals. With respect to a passive avoidance test, by means of a feature that rodents like darkness and keep in a dark place, the rodents are stimulated in the dark to escape to a bright place to acquire memory, and the passive avoidance test is a type of passive avoidance response experiments. The passive avoidance test has a short experimental period and is applicable to rapid drug screening. The scopolamine may inhibit release of acetyl choline, so as to form learning and memory disorders. The passive avoidance test is a stable learning and memory disorder modeling method and has excellent model reproducibility. The compounds Vc, Vd and Vf have a trend of decreasing the error times of the mice with memory impairment entering the darkroom and a trend of increasing the latency of the mice with memory impairment entering the darkroom, and activities of the compounds are all obviously better than the activity of the SPRC.

The invention claimed is:

1. A S-substituted-2-amino-3-mercaptopropionate derivative selected from the group of compounds consisting of:

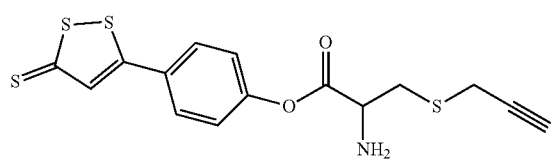
Va

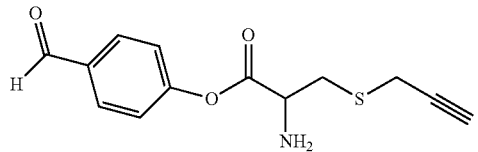
Vb

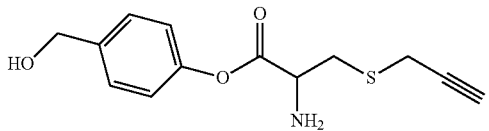
Vc

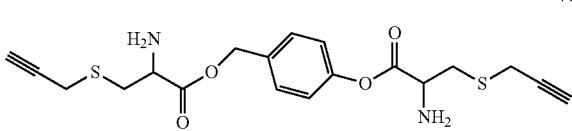
Vd

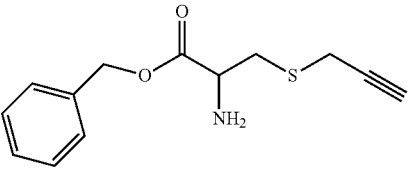
Ve

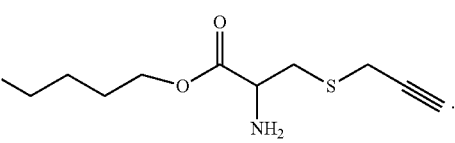
Vf

2. Any one of a medicinal acid addition salt, a solvate, a polymorphism, an enantiomer or a racemic mixture of the S-substituted-2-amino-3-mercaptopropionate derivative according to claim 1.

3. The medicinal acid addition salt of claim 2, wherein the medicinal acid addition salt is selected from salt formed by the S-substituted-2-amino-3-mercaptopropionate derivative and sulfuric acid, hydrochloric acid, hydrobromic acid, phosphoric acid, tartaric acid, fumaric acid, maleic acid, citric acid, acetic acid, formic acid, methanesulfonic acid, p-toluenesulfonic acid, oxalic acid or succinic acid.

4. A pharmaceutical composition comprising the S-substituted-2-amino-3-mercaptopropionate derivative according to claim 1 and a pharmaceutically acceptable carrier selected from the group consisting of a diluent, a flavoring agent, a solubilizer, a lubricating agent, a suspending agent, an adhesive, and an expanding agent or a medicinal addition salt thereof.

5. A pharmaceutical composition comprising any one of the medicinal acid addition salt, the solvate, the polymorphism, the enantiomer or the racemic mixture of the S-substituted-2-amino-3-mercaptopropionate derivative according to claim 2 and a pharmaceutically acceptable carrier selected from the group consisting of a diluent, a flavoring agent, a solubilizer, a lubricating agent, a suspending agent, an adhesive, and an expanding agent.

6. A method of treating a neurodegenerative disease comprising administering the S-substituted-2-amino-3-mercaptopropionate derivative according to claim 1 to a patient in need thereof.

7. The method according to claim 6, wherein the neurodegenerative disease is senile dementia.

8. A method of treating a neurodegenerative disease comprising administering any one of the medicinal acid addition salt, the solvate, the polymorphism, the enantiomer or the racemic mixture of the S-substituted-2-amino-3-mercaptopropionate derivative according to claim 2 to a patient in need thereof.

* * * * *